United States Patent [19]

Beck et al.

[11] Patent Number: 5,096,938
[45] Date of Patent: Mar. 17, 1992

[54] RADIATION-CURABLE ACRYLATES

[75] Inventors: Erich Beck, Mannheim; Wolfram Weiss, Mutterstadt; Horst Schmidt, Mannheim all of Fed. Rep. of Germany

[73] Assignee: BASF Aktiengesellschaft, Ludwigshafen, Fed. Rep. of Germany

[21] Appl. No.: 504,087

[22] Filed: Apr. 3, 1990

Related U.S. Application Data

[63] Continuation of Ser. No. 148,354, Jan. 25, 1988.

[30] Foreign Application Priority Data

Feb. 11, 1987 [DE] Fed. Rep. of Germany ....... 3704098

[51] Int. Cl.$^5$ .................. C08F 2/50; C08F 20/28; C08F 20/30
[52] U.S. Cl. .................... 522/100; 522/10; 522/103; 522/104; 522/107; 525/438; 525/530; 525/531; 525/922; 526/320
[58] Field of Search .............. 522/10, 100, 103, 104, 522/107; 525/438, 530, 531; 526/320

[56] References Cited

U.S. PATENT DOCUMENTS

| | | | |
|---|---|---|---|
| 3,952,032 | 4/1976 | Vrancken et al. | 260/404.8 |
| 4,049,634 | 9/1977 | Ko | 522/107 |
| 4,370,387 | 1/1983 | Ueno | 522/104 |
| 4,399,211 | 8/1983 | Kondo | 522/104 |
| 4,468,202 | 8/1984 | Cohen | 522/104 |
| 4,485,161 | 11/1984 | Scozzafava | 522/104 |

FOREIGN PATENT DOCUMENTS

| | | |
|---|---|---|
| 2215493 | 10/1972 | Fed. Rep. of Germany . |
| 3241264 | 5/1984 | Fed. Rep. of Germany . |
| 3316592 | 11/1984 | Fed. Rep. of Germany . |
| 3316593 | 11/1984 | Fed. Rep. of Germany . |
| 2237875 | 2/1975 | France . |
| 1362906 | 8/1974 | United Kingdom . |

Primary Examiner—Marion E. McCamish
Assistant Examiner—Arthur H. Koeckert
Attorney, Agent, or Firm—Keil & Weinkauf

[57] ABSTRACT

Radiation-curable catalysts are obtainable by reacting
A) 1 equivalent of a dihydric to hexahydric oxyalkylated $C_2$–$C_{10}$-alcohol with
B) from 0.05 to 1 equivalent of a dibasic to tetrabasic $C_3$–$C_{36}$-carboxylic acid or its anhydride and
C) from 0.1 to 1.5 equivalents of acrylic acid and/or methacrylic acid and reacting the excess carboxyl groups with an equivalent amount of epoxide compound, and are used in radiation-curable coating materials.

6 Claims, No Drawings

RADIATION-CURABLE ACRYLATES

This application is a continuation of application Ser. No. 148,354, filed on Jan. 25, 1988 now abandoned.

The present invention relates to radiation-curable acrylates, obtainable by reacting A) 1 equivalent of a dihydric to hexahydric oxyalkyated $C_2$–$C_{10}$-alcohol with B) from 0.05 to 1 equivalent of a dibasic to tetrabasic $C_3$–$C_{36}$-carboxylic acid or its anhydride and C) from 0.1 to 1.5 equivalents of acrylic acid and/or methacrylic acid and reacting the excess carboxyl groups with an equivalent amount of an epoxide compound, a process for their preparation and their use in radiation-curable coating materials.

Radiation-curable binders based on polyesters containing acrylic groups are known. Coating resins of this type are of great interest in particular for their rapid and solvent-free processibility.

The freedom of these systems from solvents saves the expense of evaporating and working the solvents. Furthermore, the danger of solvent emission is substantially reduced.

For economical processibility, in general low raw material costs and high reactivity are important with regard to the binders, as well as, in particular, a low requirement of reactive diluent for obtaining suitable processing viscosities.

DE 32 41 264 describes a possibility for dispensing with the addition of reactive diluents by using aqueous, radiation-curable binder dispersions. A radiation-curable acrylate of a particular composition which has surfactant properties and thus stabilizes the aqueous dispersions or emulsions is described for this purpose.

However, when these dispersions are used as coating materials, time has to be allowed for evaporating the water.

Low molecular weight acrylates of the polyol components of a conventional polyester acrylate resin, which are formed during an acid-catalysed esterification reaction through transesterification reactions taking place simultaneously as side reactions, likewise promote the low diluent requirement.

German Laid-Open Applications DOS 3,316,592 and DOS 3,316,593 disclose processes for the preparation of radiation-curable acrylates, in which OH-containing polyesters are esterified with excess acrylic acid, and the remaining acrylic acid is then subjected to an addition reaction with di- or polyglycidyl ethers to give non-volatile 2-hydroxy acrylates. Low molecular weight acrylates which act as diluents and can be formed from components of the polyester by transesterification remain in the end product. However, a considerable disadvantage of such compounds is their high toxicity and volatility, which low molecular weight acrylates in particular are known to exhibit.

It is an object of the present invention to provide novel radiation-curable acrylates for radiation-curable coating materials, which have substantially lower contents of volatile and physiologically unacceptable acrylic compounds, whose requirement of reactive diluents is very low and which can be processed to give high quality coatings.

We have found that this object is achieved by radiation-curable acrylates, obtainable by reacting A) 1 equivalent of a dihydric to hexahydric oxyalkylated $C_2$–$C_{10}$-alcohol with B) from 0.05 to 1 equivalent of a dibasic to tetrabasic $C_3$–$C_{36}$-carboxylic acid or its anhydride and C) from 0.1 to 1.5 equivalents of acrylic acid and/or methacrylic acid and reacting the excess carboxyl groups with an equivalent amount of an epoxide compound.

Suitable components (A) are oxyethylated, oxypropylated and mixed oxyethylated and oxypropylated dihydric to hexahydric alcohols, such as the diols ethylene glycol, propylene glycol, butane-1,4-diol, pentane-1,5diol, neopentylglycol, hexane-1,6-diol, 2-methylpentane-1,5-diol, 2-ethylbutane-1,4-diol, dimethylolcyclohexane and 1,1'-isopropylidenebis-(p-phenyleneoxy)-di-3-ethanol, triols, such as glycerol, trimethylolethane, trimethylolpropane and trimethylolbutane, tetraols, such as pentaerythritol and ditrimethylolpropane, and hexols, such as erythritol and sorbitol. Trihydric to hexahydric oxyalkylated $C_3$-$C_6$-alcohols, such as oxyethylated and/or oxypropylated trimethylolpropane, glycerol, pentaerythritol and sorbitol, are preferred.

The degree of oxyalkylation is as a rule from 1 to 30, preferably from 2 to 10.

Suitable components (B) are dibasic to tetrabasic $C_3$–$C_{36}$-carboxylic acids or their anhydrides, such as succinic acid, succinic anhydride, glutaric acid, glutaric anhydride, adipic acid, sebacic acid, phthalic acid, phthalic anhydride, terephthalic acid, maleic acid, maleic anhydride, fumaric acid, citraconic acid, tetrahydrophthalic acid, tetrahydrophthalic anhydride, hexahydrophthalic acid, hexachloroendomethylenetetrahydrophthalic acid, dimeric linoleic acid, trimellitic acid, trimellitic anhydride, pyromellitic acid and pyromellitic anhydride. Adipic acid, phthalic acid, phthalic anhydride, maleic anhydride and fumaric acid are preferred.

Suitable mono-, di- or polyepoxide compounds, preferably di- and triepoxide compounds, are epoxidized olefins, glycidyl esters of saturated or unsaturated carboxylic acids or glycidyl ethers of aliphatic or aromatic polyols. The glycidyl ethers of butanediol, bisphenol A and pentaerythritol are preferred.

The esterification of the components (A), (B) and (C) is carried out by well known methods, in the presence of an acidic esterification catalyst, such as sulfuric acid or para-toluenesulfonic acid, which is used in an amount of from 0.1 to 3% by weight, based on components (A), (B) and (C), at from 60° to 140° C., the water formed being removed azeotropically. Suitable entraining agents are aliphatic and aromatic hydrocarbons, for example alkanes and cycloalkanes, such as n-hexane, n-heptane and cyclohexane, aromatics, such as benzene, toluene and xylene isomers, and special gasolines which have boiling points from 70° to 140° C. Particularly preferred entraining agents are cyclohexane and toluene. The amount of hydrocarbon added is not critical; depending on the apparatus used, the amount added may vary from 0.1 times to twice the amount of reaction mixture of the components (A), (B) and (C). A ratio of reaction mixture to hydrocarbon of from 1:0.2 to 1:0.8 is particularly advantageous. The solvent used is removed from the reaction mixture after the esterification, if necessary under reduced pressure.

The esterification is carried out to a conversion of not less than 85%, preferably from 90 to 95%.

To avoid premature polymerization, the esterification is advantageously effected in the presence of small amounts of inhibitors. These are the conventional compounds used for preventing thermal polymerization, for example compounds of the hydroquinone, hydroquinone monoalkyl ether, 2,6-di-tert-butylphenol, N-nitrosamine, phenothiazine or phosphite type. They are used in general in amounts of from 0.001 to 2.0, preferably from 0.005 to 0.5, % by weight, based on the sum of the components (A), (B) and (C).

The ratio of the number of equivalents of components (A):(B):(C) is 1:0.05–1:0.1–1.5, preferably 1:0.1–0.6:0.5–0.9. From 1 to 1.5, preferably from 1.1 to 1.25, equivalents of acrylic acid and/or methacrylic acid are used per equivalent of the theoretical reaction product of (A) and (B).

After the esterification, the esterification catalyst is generally neutralized in a suitable manner, for example by adding a tertiary amine or an alkali metal hydroxide. The carboxyl groups of the acrylate resin and the excess acrylic acid or methacrylic acid are reacted with an amount, equivalent to their acid number, of one of the abovementioned epoxide compounds at from 90 to 130° C. preferably from 100 to 110° C., until the acid number falls below 5 mg of KOH/g. The reaction between carboxyl and epoxy groups can be catalysed using suitable compounds, such as tertiary amines, quaternary ammonium compounds or Lewis bases, for example of the thiodiglycol type. The novel acrylates have viscosities of, for example, from 0.5 to 20, preferably from 1 to 15, Pa.s at 23° C.

The acrylates prepared according to the invention are processed in general by adding further reactive diluents known in connection with radiation curing. 4-tertbutylcyclohexyl acrylate, phenoxyethyl acrylate, hexanediol diacrylate, tripropylene glycol diacrylate, trimethylolpropane diacrylate and acrylates of oxyalkylated diols and triols are mentioned here merely by way of example. The coating materials prepared by the novel process are advantageously crosslinked by electron beams or, after the addition of a photoinitiator, by UV radiation, and give films which completely meet practical requirements.

EXAMPLE 1

532.6 g of oxyethylated trimethylolpropane having an OH number of 630 mg of KOH/g, 98 g of maleic anhydride, 316.8 g of acrylic acid, 437.7 g of cyclohexane, 4.73 g of sulfuric acid, 2.93 g of hydroquinone monomethyl ether, 0.95 g of 2,6-di-tert-butylcresol, 0.95 g of 50% strength by weight hypophosphorous acid and 0.028 g of phenothiazine were combined and heated at the boil. 93 g of water were distilled off in the course of about 11 hours, after which the solvent too was removed by distillation. The reaction mixture had an acid number of 38.8 mg of KOH/g. Thereafter, 105.7 g of diglycidyl ether of bisphenol A (epoxide equivalent weight 186 g/mole) and 17.9 g of tributylamine were added. The reaction was continued at from 105 to 110° C. until an acid number of 4.4 mg of KOH/g was reached, this taking about 8 hours. The viscosity at 23° C. was 4.3 Pa.s.

EXAMPLE 2

The two-stage procedure described in Example 1 was used and the following compounds were reacted:

1st stage:

532.6 g of oxyethylated trimethylolpropane (OH number 630 mg/g)
116.1 g of fumaric acid
316.8 g of acrylic acid
482.7 g of cyclohexane
4.82 g of sulfuric acid
2.99 g of hydroquinone monomethyl ether
0.96 g of 2,6-di-tert-butylcresol
0.96 g of hypophosphorous acid (50% strength by weight)
0.96 g of triphenyl phosphite
0.029 g of phenothiazine
Amount of water distilled off: 110 ml
Acid number: 51.0 mg of KOH/g 2nd stage 120.5 g of diglycidyl ether of bisphenol A (epoxide equivalent weight 186 g/mole)
18.2 g of tributylamine
Product viscosity (23° C.): 12.8 Pa.s.

EXAMPLE 3

The two-stage procedure described in Example 1 was used and the following compounds were reacted:

1st stage 532.6 g of oxyethylated trimethylolpropane (OH number 630 mg/g)
146.1 g of adipic acid
316.8 g of acrylic acid
497.8 g of cyclohexane
4.98 g of sulfuric acid
3.10 g of hydroquinone monomethyl ether
0.99 g of 2,6-di-tert-butylcresol
0.99 g of hypophosphorous acid (50% by weight)
0.99 g of triphenyl phosphite
0.033 g of phenothiazine
Amount of water distilled off: 111 ml
Acid number: 37.9 mg of KOH/g 2nd stage 106.9 g of diglycidyl ether of bisphenol A (epoxide equivalent weight 186 g/mole)
18.8 g of tributylamine
Product viscosity (23° C.): 2.6 Pa.s.

EXAMPLE 4

The two-stage procedure described in Example 1 was used and the following compounds were reacted:

1st stage:

623.3 g of oxypropylated and oxyethylated trimethylolpropane (PO:EO =86:14; OH number =540 mg of KOH/g)
98.0 g of maleic acid
316.8 g of acrylic acid
525.1 g of cyclohexane
5.20 g of sulfuric acid
1.04 g of hydroquinone monomethyl ether
1.04 g of 2,6-di-tert-butylcresol
1.04 g of hypophosphorous acid
1.04 g of tin dichloride hydrate
0.52 g of phenothiazine
Amount of water distilled off: 85 ml
Acid number: 48.5 mg of KOH/g 2nd stage 128.1 g of pentaerythritol triglycidyl ether (epoxide equivalent weight 163 g/mole)
18.8 g of tributylamine
Product viscosity (23° C.): 5.36 Pa.s In the case of the products from Examples 1 to 4, no volatile diol acrylates were detected by gas chromatography. Acrylates derived from the trimethylolpropane were found to be present in an amount less than 0.8% by weight.

COMPARATIVE EXAMPLE 1

780 g of adipic acid, 420 g of phthalic anhydride, 600 g of ethylene glycol and 560 g of trimethylolpropane were combined, and heated at 160° C. Thereafter, the temperature was increased to 210° C. and the esterification was continued under reduced pressure until an acid number of 0.6 mg of KOH/g was reached. The product had an OH number of 320 mg of KOH/g. 582 g of acrylic acid, 916 g of cyclohexane, 5.5 g of sulfuric acid, 1.8 g of methylhydroquinone monomethyl ether, 0.9 g of 2,6-di-tertbutylcresol and 0.04 g of phenothiazine were added to 1,250 g of the said product. Thereafter, further water was distilled off (138 g of water in 10 hours). After the solvent had been removed by distillation, the reaction mixture had an acid number of 44 mg of KOH/g. 10.5 g of dimethylethanolamine, 192 g of pentaerythritol triglycidyl ether and 1 g of thiodiglycol were then added, and the reaction was continued at from 105° to 110° C.. After 5 hours, an acid number of 2.6 mg of KOH/g was reached. The viscosity (23° C.) was 47.5 Pa.s.

The following amounts of acrylates of glycol and trimethylolpropane were detected by gas chromatographic measurements:

1.0% of hydroxyethyl acrylate
3.8% of ethylene glycol diacrylate
1.9% of trimethylolpropane acrylates

Testing the coating properties

After dilution to a processing viscosity and the addition of a photoinitiator or a photoinitiator combination, the products prepared as described in the Examples were applied in a 100 μm layer (wet film thickness) onto glass and conveyed, at a distance of about 10 cm, past a medium pressure mercury lamp having a power of 80 W/cm. Exposure was effected in the air. The numerical value given in Table 1 for the reactivity indicates the belt speed at which a scratch-resistant coating was obtained.

TABLE 1

| Polyester acrylate prepared by Example (per 100 g) | Coating tests | | | | Comparative Example 1 |
|---|---|---|---|---|---|
| | 1 | 2 | 3 | 4 | |
| hexanediol diacrylate (g)[1] | 25.3 | 41.6 | 21.4 | 31.6 | 53.8 |
| Hexanediol diacrylate content (%)[1] | 20.2 | 29.4 | 17.6 | 24.0 | 35.0 |
| Benzil dimethyl ketal | 1.25 | 1.42 | 1.21 | 1.32 | 1.54 |
| Benzophenone | 2.50 | 2.84 | 2.42 | 2.64 | 3.08 |
| Methyldiethanolamine | 3.75 | 4.26 | 3.63 | 3.96 | 4.62 |
| Volatile components (%) | 3.4 | 3.2 | 3.0 | 2.9 | 7.1 |
| Reactivity (m/min) | 35 | 30 | 50 | 25 | 45 |
| Pendulum hardness (DIN 53,157) | 76 | 97 | 39 | 53 | 42 |

[1]Corresponding to a set viscosity of 100 sec efflux time according to DIN 4 at 23° C.

We claim:
1. A radiation-curable acrylate, consisting essentially of 1) the co-esterification reaction product of the following three components,
   A) 1 equivalent of a dihydric to hexahydric oxyalkylated, $C_2$–$C_{10}$-alcohol with
   B) from 0.05 to 1 equivalent of a dibasic to tetrabasic $C_3$–$C_{36}$-carboxylic acid or its anhydride and
   C) from 0.1 to 1.5 equivalents of acrylic acid and/or methacrylic acid the resulting co-esterification product having free carboxyl groups, reacted with 2) an epoxide compound, the amount of epoxide groups on the epoxide compound being sufficient to react with the free carboxyl groups present in the co-esterification reaction product and with unreacted acrylic acid or methacrylic acid from said co-esterification reaction.

2. A radiation-curable acrylate as defined in claim 1, wherein the epoxide compound is a glycidyl ether of butanediol, bisphenol A or pentaerythritol.

3. A radiation-curable acrylate as defined in claim 1, wherein a trihydric to hexahydric oxyalkylated $C_3$–$C_6$-alcohol is used as component (A).

4. A radiation-curable acrylate as defined in claim 1, wherein an oxyalkylated alcohol having a degree of 1 to 30 is used as component (A).

5. A radiation-curable acrylate as defined in claim 1, wherein the components (A), (B) and (C) have a conversion of not less than 85%.

6. A radiation-curable coating material containing a radiation-curable acrylate as defined in claim 1.

* * * * *